United States Patent [19]
Robinson et al.

[11] Patent Number: 5,646,350
[45] Date of Patent: Jul. 8, 1997

[54] MONITORING SLOW SPEED MACHINERY USING INTEGRATOR AND SELECTIVE CORRECTION OF FREQUENCY SPECTRUM

[75] Inventors: James C. Robinson; Ronald G. Canada, both of Knoxville, Tenn.

[73] Assignee: Computational Systems Inc., Knoxville, Tenn.

[21] Appl. No.: 590,340

[22] Filed: Jan. 23, 1996

[51] Int. Cl.$^6$ .................................................. G01N 29/00
[52] U.S. Cl. ............................................ 73/602; 73/599
[58] Field of Search ............................ 73/579, 599, 602, 73/658

[56] References Cited

U.S. PATENT DOCUMENTS

| | | | |
|---|---|---|---|
| 4,429,578 | 2/1984 | Darrel et al. | 73/659 |
| 4,520,674 | 6/1985 | Canada et al. | |
| 4,612,620 | 9/1986 | Davis et al. | 73/570 |
| 4,683,542 | 7/1987 | Taniguti | 73/602 |
| 4,862,407 | 8/1989 | Fette et al. | |
| 4,885,707 | 12/1989 | Nichol et al. | |
| 4,929,874 | 5/1990 | Mizuno et al. | |
| 5,058,434 | 10/1991 | Zaschel | 73/659 |
| 5,255,565 | 10/1993 | Judd et al. | |

OTHER PUBLICATIONS

James C. Robinson, Francis E. LeVert, and J.E. Mott; "Vibration Data Acquisition of Low Speed Machinery ($\geq 10$ rpm) Using a Portable Data Collector and a Low Impedance Accelerometer"; 1992–1993.

J.C. Robinson, F.E. LeVert, and J.E. Mott; "Vibration Measurements on Low Speed Machinery Using an Industrial Grade Accelerometer"; 1992–1993.

CSI Model 2115 User's Manual, May, 1992.

*Primary Examiner*—George M. Dombroske
*Assistant Examiner*—Max H. Noori
*Attorney, Agent, or Firm*—Luedeka, Neely & Graham, P.C.

[57] ABSTRACT

A method for nonintrusive monitoring of slow speed machinery incorporates a high sensitivity accelerometer capable of detecting low level mechanical vibrations, and a standard data collector/analyzer for processing the accelerometer output in accordance with a slow speed technology (SST) methodology that is implemented by firmware or software. To prevent the high frequency components from overwhelming the low frequency components of the accelerometer output as a result of dynamic range loss during processing of the accelerometer output by the data collector/analyzer, the SST methodology converts the accelerometer output from the acceleration domain to the velocity domain with an analog integrator that amplifies the low frequency components of the accelerometer output while attenuating the high frequency components. The analog integrator distorts the low frequency vibration components as well as the electrical noise introduced by the accelerometer. The distorted signal is then digitized by an A/D converter and transformed to the frequency domain by means of a fast Fourier transform. Within the frequency domain, mechanical vibrations (significant peaks) are separated from the noise and other non-vibration induced transients by fitting the transformed data set to a threshold noise floor that is calculated based on a statistical variance of a most probable noise floor of the accelerometer. All peaks/amplitudes greater than the threshold noise floor are considered significant and retained as indicative of mechanical vibrations occurring within the machinery, while all peaks below the threshold noise floor are considered insignificant and eliminated from further consideration.

10 Claims, 5 Drawing Sheets

MONITORING SLOW SPEED MACHINERY USING INTEGRATOR AND SELECTIVE CORRECTION OF FREQUENCY SPECTRUM

TECHNICAL FIELD

The present invention relates to nonintrusive monitoring and fault detection of slow speed machinery. More particularly, it relates to a method and apparatus for determining the condition of a machine operating at slow speed by amplifying low frequency components and attenuating high frequency components within the velocity domain.

BACKGROUND

There are a number of applications in today's industrial and manufacturing environments for machines that operate at slow speed. The efficient operation and maintenance of these machines is essential to maximizing production and minimizing downtime. Latent or incipient failures of these machines often go undetected due to the difficulty in visually detecting faults such as a divot or flat spot in a slow speed bearing.

There are known techniques for monitoring medium and high speed machinery by analyzing mechanical vibrations generated by the machinery during operation. An accelerometer is typically used to generate a signal corresponding to the vibrations produced by the machine as it operates. The signal produced by the accelerometer will include normal (nonfault) vibration components as well as fault related vibration components occurring within the machine. Various analytic techniques are then used to separate the vibration signal into its constituent components and identify those components corresponding to possible faults and other mechanical vibrations.

Unfortunately, the techniques which are used to monitor for faults within medium and high speed machinery are not equally effective for monitoring faults within slow speed machinery. There is a special difficulty in monitoring low rpm vibration produced by low speed machines because the low frequency components will typically be of lesser amplitude than the higher frequency components. The higher amplitude, higher frequency components of the vibration signal will tend to drown out the low amplitude, low frequency vibrations of interest, producing an unacceptably high signal-to-noise ratio. Further complicating the processing of vibration signals produced by slow speed machines is that the sensor (accelerometer) adds an electrical noise component to the composite signal. The problem for the monitoring system becomes one of extracting the low level components (requires a wide dynamic range) from the composite signal and then differentiating the vibration components of interest from the other low level components generated from electrical noise sources, temperature transients, and other similar sources of irrelevant components. Thus, the analysis of the vibration signal must become more sensitive to the low level (and often low frequency) components when monitoring slow speed machinery. Existing analysis techniques are unable to effectively adjust to these higher sensitivity requirements and process the vibration signal without eliminating the low level components.

The sensitivity required of the sensor is based on the amount of displacement to be sensed. For high sensitivity applications, the sensor of choice for vibration analysis is typically an accelerometer having a dynamic range of between 100 to 120 dB. It is desirable that the analysis method be able to accommodate this range. Most analysis methods, however, result in an attenuation of the accelerometer signal so that the dynamic range of the analyzed signal is, for example, reduced to about 80 dB. Thus, there is a need for a measurement system having a dynamic response that is at least as good as that of the accelerometer.

Although there are no universally-accepted criteria for classifying machinery as slow speed, intermediate speed, or high speed, it is generally recognized that slow speed machines are those that operate at or below 600 rpm. The value of 600 rpm is significant because it represents the approximate speed at which alert levels relative to vibration in the velocity domain must be reduced as the speed of the machine decreases. A commonly accepted methodology is to establish alert levels which decrease linearly with decreasing speed (or constant in the displacement domain).

Thus, there is a need for a reliable and effective measurement system for monitoring slow speed machinery that is capable of differentiating fault-induced vibration components from machinery-induced vibration components as well as other extraneous components, including electrical noise and transients. The system should be minimally responsive to temperature transients and maintain a wide dynamic range.

SUMMARY

The present invention discloses a method of processing vibration signals to produce information corresponding to mechanical vibration in slow speed machinery. The method includes the steps of producing a vibration signal measured in acceleration units corresponding to mechanical vibration generated by slow speed machinery. The vibration signal measured in acceleration units is sent through a practical analog integrator which produces a distorted signal in velocity units. The distortion is introduced by the inclusion of high pass filters in front of the analog integrator which are employed to keep the low frequency signals from exceeding the limitations imposed by the instrument processing the data. Relative to the original signal in acceleration (g) units, the output signal from the analog integrator at higher frequencies are attenuated and those at lower frequencies are amplified. The frequency where the output signal is the same as the input signal is referred to as the pivot frequency. Scaling the output of the integrator to be in "inches per second" units from an input in g units, the pivot frequency is 61.5 Hz. The output in velocity units from the integrator is distorted at low frequencies (relative to the pivot frequency) due to practical limitations on the integrator, thereby producing a distorted vibration signal measured in velocity units.

The distorted vibration signal is digitized during a predetermined time interval to produce a time series of digital vibration signals measured in velocity units. A first preliminary output in the frequency domain is produced to correspond to the time series of digital vibration signals. A most probable noise floor is calculated, and the amplitudes of the first preliminary output are compared to the most probable noise floor. A second preliminary output is produced by eliminating amplitudes in the first preliminary output that are below the most probable noise floor. Finally, the second preliminary output is corrected by a correction function that inversely corresponds to the distorting of the analog integration to produce a final output corresponding to mechanical vibration generated by the slow speed machinery.

To calculate the most probable noise floor, a plurality of minimum amplitudes in a plurality of segments of the first preliminary output may first be determined. The minimum amplitudes within the first preliminary output are fitted with a quadratic function to produce a quadratic fit curve. One standard deviation is then added to the quadratic fit curve at all frequencies to produce the most probable noise floor.

The first preliminary output may be produced by converting the time series of digital vibration signals to the frequency domain, producing a distorted vibration spectrum. To accomplish this step, the time series of digital vibration signals may be transformed to the frequency domain by means of a fast Fourier transform, producing a series of spectra. A single spectrum is then produced from the series of spectra. Each single spectrum, which may be produced by averaging the series of spectra, includes a plurality of amplitudes corresponding to a unique one of the frequencies. The amplitudes correspond to mechanical vibration produced by the slow speed machinery, and noise.

The method may further include the step of calculating a threshold noise floor based on a statistical variance of the most probable noise floor. The statistical variance is preferably based on a three sigma statistical variance of the most probable noise floor.

The method may further include the step of eliminating a predetermined range of frequencies and corresponding amplitudes from the distorted vibration signal. Alternatively, the method may include the step of eliminating a predetermined range of frequencies and corresponding amplitudes from the vibration signal.

Finally, the vibration signal may be distorted by double integrating the vibration signal, thereby producing the distorted vibration signal as measured in displacement units.

BRIEF DESCRIPTION OF PREFERRED EMBODIMENTS

The preferred embodiments of the invention will now be described in further detail with reference to the drawings wherein like reference characters designate like or similar elements throughout the several drawings as follows.

DETAILED DESCRIPTION OF PREFERRED EMBODIMENTS

Figure 1:
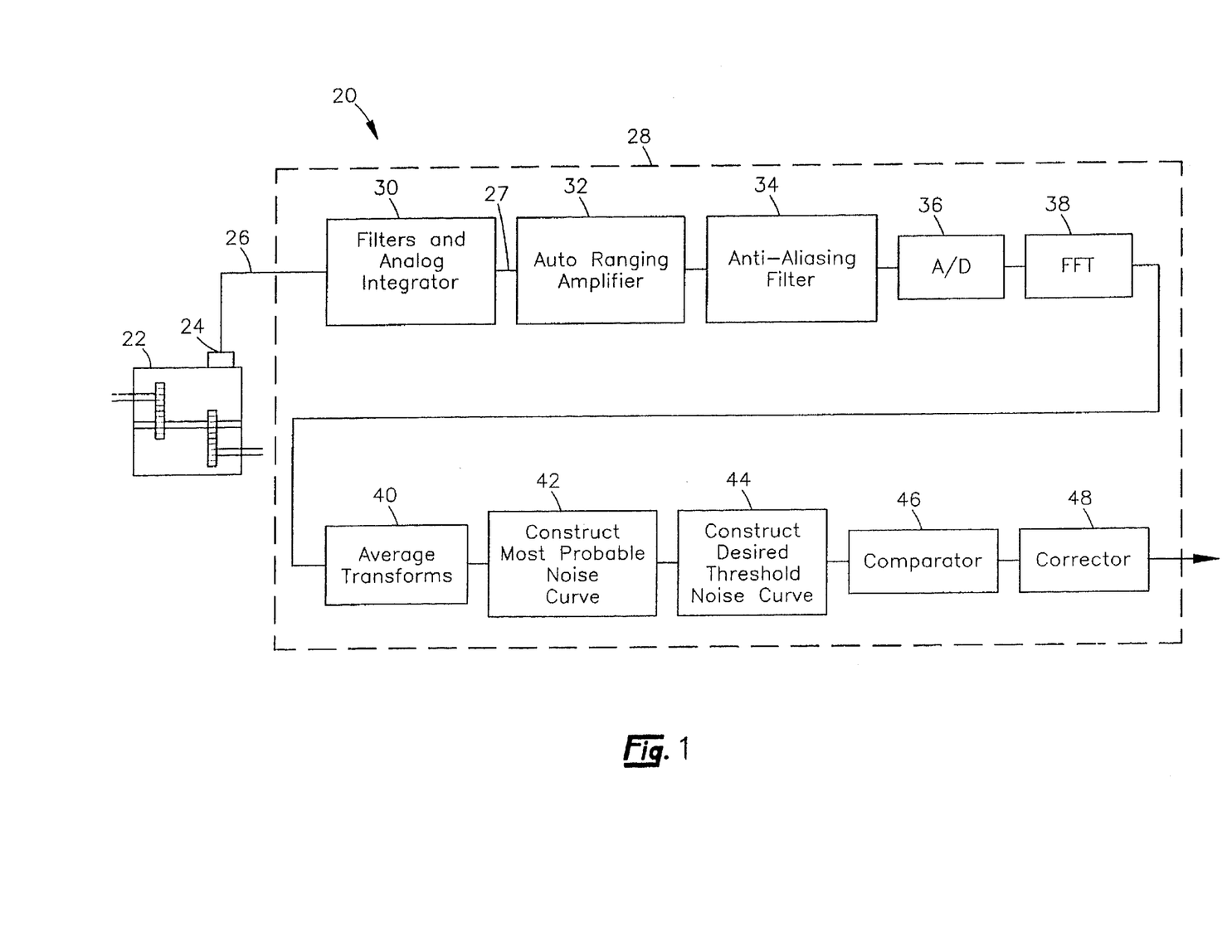
FIG. 1 is a functional block diagram of a preferred embodiment of the slow speed technology (SST) methodology implemented in a portable data collector/analyzer.

When monitoring vibrations on slow speed machinery (i.e., 600 rpm or less) using an accelerometer (vibration transducer), the vibration signal levels at the turning speed are generally of low amplitude. Low level signals of interest often become buried within the composite signal that includes significantly higher frequency, higher amplitude components that are of little or no relevance. The vibration measurement and analysis system of FIG. 1 illustrates a preferred embodiment of the slow speed technology (SST) methodology of the present invention. This SST methodology extracts the low level components from the composite signal and differentiates the components of interest from unwanted low level components produced by various noise sources. A component of interest is one that is produced by a vibration-inducing event within the machinery.

As shown in FIG. 1, a system 20 for measuring vibrations produced by a slow speed machine 22 includes a vibration transducer (sensor), or accelerometer 24, cabling 26, and a data collector/analyzer 28. The accelerometer 24 is positioned on the machine 22 while the machine is operating. Vibrations produced by the machine 22 are sensed by the accelerometer 24 and provided to the analyzer 28 in the form of analog voltages via cable 26. In a preferred embodiment, the accelerometer 24 is a low impedance sensor which employs shear mode technology, has a mechanical sensitivity of 500 mV/g, a resonance frequency of greater than 10 kHz, and low electrical noise in the internal electronics. By selecting an accelerometer 24 having a sensitivity of 500 mV/g, the SST methodology presented herein can be used to monitor machines operating as slow as 10 rpm with as little as 10 mils p—p vibration.

The sensitivity required for monitoring the machine 22 is based on displacement, and the accelerometer output (relative to constant displacement) is proportional to the square of frequency. Therefore, the particular accelerometer 24 employed will depend on the speed of the particular machine 22 that is being monitored. For example, a required sensitivity of 5 mils from a machine operating at 20 rpm will provide an acceleration level of 1/100th of that from a machine operating at 200 rpm for the same 5 mil sensitivity level. It will be appreciated that for any particular accelerometer 24, there is a speed at which the signal generated by the vibration of the machine 22 cannot reliably be separated from non-vibration excitation such as electrical noise generated within the measurement and analysis system 20.

The signal-to-noise ratio of the vibration signal received by the analyzer 28 on cable 26 is established within the accelerometer 24 as the sensor element output is converted from an electrical charge to an analog voltage. As discussed above, the signal output of the accelerometer 24 will vary in relation to the square of frequency ($f^2$), and at low frequency noise will vary inversely with frequency ($1/f$). Therefore, the signal-to-noise ratio will vary proportionally with frequency cubed ($f^3$). The ceramic sensing material is preferable over quartz due to the high sensitivity requirements of the accelerometer 24. The conversion to voltage must be efficient at very low frequency (in the 0.1 Hz range) which results in a charge converter being preferable to a voltage follower. The sensor should be rugged, economical, and applicable to a wide range of industrial applications. Therefore, a preferred accelerometer 24 is one having a sensitivity of between 0.5 to 1.0 V/g and a resonant frequency greater than 10 KHz.

To minimize the potential for noise being introduced by the cable 26, the cable 26 is preferably either a coaxial cable or twisted pair. If a twisted pair is employed, it should be shielded with the shield attached to signal return at both ends to reduce the potential for RF contributions to the signal. The cable should be chosen to minimize the potential for EMI, and it should minimize the potential for dynamic forces applied to the accelerometer 24 to effect the signal. In this regard, a coiled cable hanging from the accelerometer 24 can easily get into a low frequency oscillation mode causing a low frequency dynamic force to be applied to the accelerometer 24. If a coiled cable is used, it should be clamped near the accelerometer 24 so that the cable can not induce a low frequency force on the accelerometer 24 due to the cable tending to oscillate when hanging from the accelerometer 24.

A typical accelerometer has a dynamic range of between 100 to 120 dB. For monitoring of slow speed machinery, the analyzer 28 must be able to accommodate this range. The analyzer 28 ultimately converts the analog voltage signal on cable 26 to digital format for processing. Normally, to process the digitized vibration signal with full dynamic range would require a 20 to 22 bit analog-to-digital (A/D) converter. Such an A/D converter is not readily available as an integral part of a data collector/analyzer 28. For intermediate speed machinery, the full 100 to 120 dB dynamic range is seldom required and so a more practical A/D converter (12 to 16 bit) is acceptable. Slow speed machinery, however, frequently drives equipment that emits large amplitude, high frequency signals which are intermixed with the lower amplitude, lower frequency signals of interest. To prevent the low frequency components of the vibration signal from being overwhelmed by the higher frequency components and lost during the processing, the high frequency signals must be removed or at least attenuated prior to processing. If the high frequency signals are not attenuated, bit stutter produced by the A/D converter 36 will be the controlling noise source. It has been determined that analog integration of the vibration signal provides a convenient method for attenuating high frequency components while amplifying the low frequency components. Practical analog integrators distort the low frequency components, but that distortion is deterministic and, therefore, correctable.

As discussed above, the dynamic range of the analyzer 28 is adversely affected by high frequency signal components generated by the accelerometer 24. To illustrate how analog integration improves the dynamic range of the analyzer 28, consider a machine turning at 20 rpm with 5 mils p—p vibration and a large component at 200 Hz. An ideal integrator (shown at 56 in FIG. 2) would provide an improvement of approximately 55 dB. This value represents a gain of 45 dB at 20 rpm and an attenuation of 10 dB at 200 Hz. A practical integrator (includes resistor $R_3$ in FIG. 2) will not provide the full 55 dB theoretical improvement due to the effect of high pass filtering within the integrator 56, but an improvement of 25 to 35 dB is obtainable.

In a preferred embodiment, the analyzer 28 is a CSI 2120 data collector/analyzer which performs all of the required processing and analysis of the vibration signal produced by the accelerometer 24. To avoid necessitating a hardware change to the analyzer 28, the SST methodology of the present invention is implemented with firmware or software.

Figure 2:
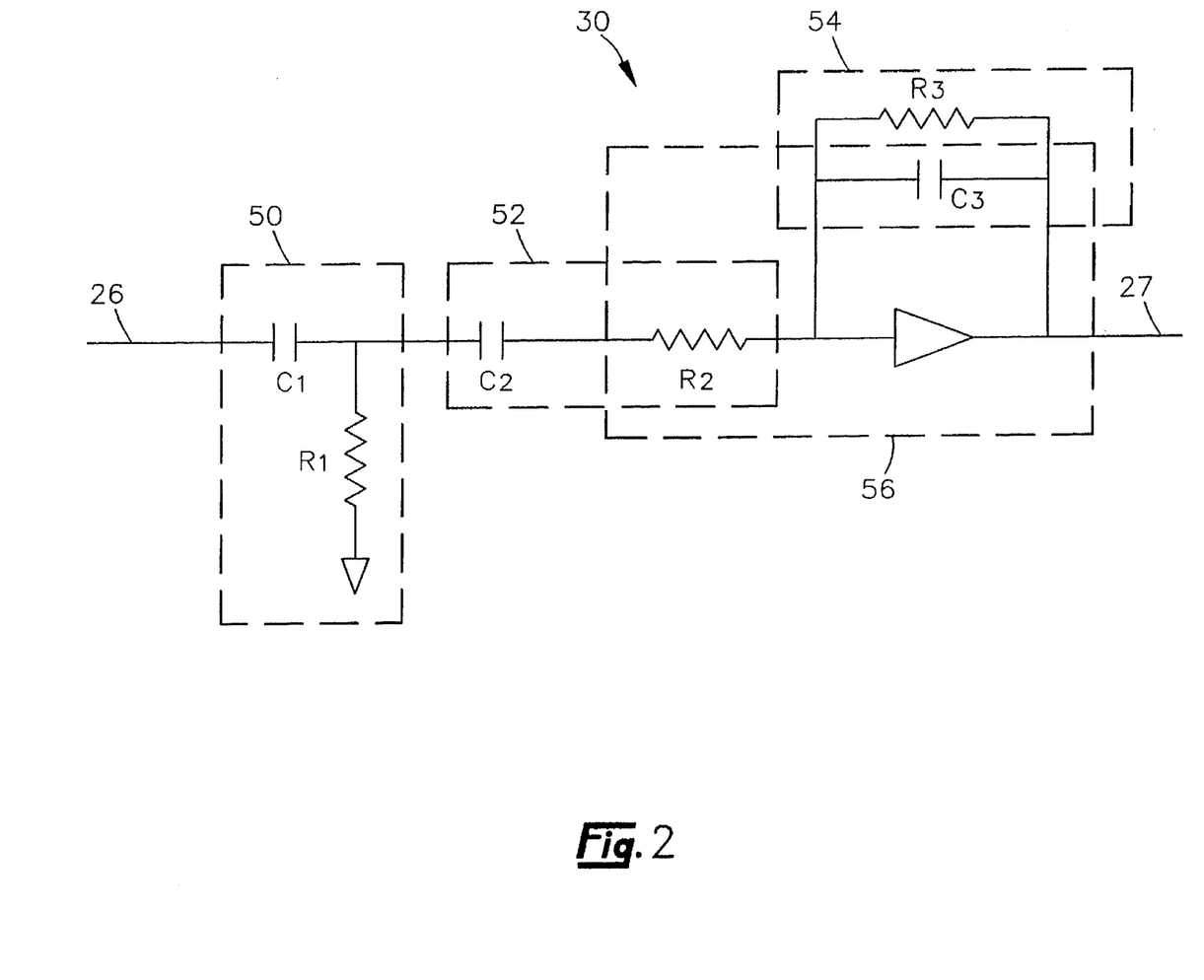
FIG. 2 is a schematic diagram of the high pass filters and analog integrator illustrated in block form in FIG. 1.

Within the analyzer 28, the vibration signal on cable 26 is converted from the acceleration domain to the velocity domain by filters and analog integrator 30. FIG. 2 provides a schematic diagram of the filters and analog integrator 30, which includes a first single pole, high pass filter 50 preferably having a 3 dB point of 0.5 Hz, a second single pole, high pass filter 52 preferably having a 3 dB point of 2.4 Hz, a third single pole, high pass filter 54 preferably having a 3 dB point of 1.6 Hz, and an analog integrator 56. The gain of the integrator 56 is given by the equation:

$$\text{Gain} = \frac{1}{R_2 C_3} . \quad (1)$$

In the frequency or spectral domain, the gain given by equation (1) is inversely proportional to frequency, and it can be changed by changing the $R_2$ and $C_3$ parameters. With proper gain setting for the integrator 56, the output signal on line 27 is velocity in ips (inches per second) given that the signal on line 26 from the accelerometer 24 is in g units. With these units, the gain is unity at 61.5 Hz (the pivot frequency/point). The lower frequency components of the vibration signal are attenuated somewhat in the velocity domain due to the high pass filtering necessary for the analog integrator 56. However, the total effect of the analog integrator 56 is to attenuate the high frequency components above the pivot frequency and amplify the low frequency components below the pivot frequency in the velocity domain. Therefore, the analog integrator 56 distorts the low frequency components measured in velocity units in a deterministic manner, which distortion can be corrected analytically.

In the spectral domain, the spectral data can be easily corrected by multiplying the observed spectral magnitude by the inverse of the attenuation introduced by the three filters 50–54. The magnitude of the attenuation factor at any frequency is given by the equation:

$$Att(f) = \frac{f^3}{\sqrt{f^2 + F_{B_1}^2} \sqrt{f^2 + f_{B_2}^2} \sqrt{f^2 + f_{B_3}^2}} \quad (2)$$

where:

$f_{B1}$ is the break (cutoff) frequency for the first high pass filter;

$f_{B2}$ is the break frequency for the second high pass filter; and $f_{B3}$ is the break frequency for the third high pass filter.

The observed spectral data (in the velocity domain) will be corrected for attenuation only at those specific frequency points where the data is determined from statistical analysis to be introduced by machinery vibrations.

The distorted signal produced by the analog integrator 56 is preferably received by an autoranging amplifier 32 which amplifies all components of the distorted signal based on the strongest component of the signal. It will be appreciated that the strongest point of the signal, generally a high frequency point, has been significantly reduced relative to the case where the analog integrator 56 was not employed. In an alternate embodiment, the autoranging amplifier 32 is eliminated and the accelerometer 24 produces a vibration signal having sufficient strength for electronic processing by the analyzer 28.

To prevent anti-aliasing during the digitization process, the signal is passed through an anti-aliasing filter 34, which is typically a steep low pass filter, before being digitized by A/D converter 36. The A/D converter 36 will have "bit stutter" of one or two bits, thereby producing a noise floor that is substantially white. Therefore, the A/D converter 36 represents another potential source of dynamic range loss. To prevent dynamic range loss within the A/D converter 36, a high bit resolution converter is required where all bits are distributed evenly between the $V_{ref}$ of the converter 36. The practical limit on A/D converters is 16 to 18 bits, which represents a 24 to 30 dB improvement in dynamic range relative to a 12 bit A/D converter. Therefore, the dynamic range needed to monitor slow speed machinery is obtained through a combination of a high resolution A/D converter 36 with minimal bit stutter and an analog integrator 56.

A time series of digital signals produced by A/D converter 36 over a predetermined time interval is transformed to the frequency domain by means of a fast Fourier transform 38. Preferably, a time series of fast Fourier transforms are taken and averaged by averager 40 to produce an average transformation to the frequency domain. Averaging a series of transformations is useful for reducing the statistical variations introduced by extraneous noise sources.

The frequency spectrum of the transformed signal is analyzed to determine the significance of the amplitudes. A significant peak amplitude is one that is likely introduced by vibrations within the machinery and, for purposes of peak detection, significant amplitudes include those amplitudes that are within a predetermined range of frequencies on either side of a significant peak. In a preferred embodiment, a minimum of three data points, or amplitudes, are required for peak detection. Therefore, the predetermined range of frequencies must be large enough to include at least one data point on each side of the peak.

Statistical noise analysis concepts are employed to separate the mechanical induced signal components (significant amplitudes) from the randomly varying noise introduced by the accelerometer 24, such as electrical induced noise and temperature induced noise. The procedure is to determine the most probable noise floor (that noise floor which would exist after many averages), as generally indicated at 42 in FIG. 1, and then add to the most probable noise floor a threshold level, indicated generally at 44 in FIG. 1, such that a signal component which exceeds the threshold can be assumed to be vibration induced with a specified confidence level. For example, when specifying a confidence level of 95% one would add to the most probable noise floor three standard deviations to establish the 95% confidence level threshold.

The theoretical lower level of the noise floor (in the g domain), or fundamental noise floor, is a property of the sensor 24 (usually specified in units of g's/Hz$^{1/2}$ at 1 Hz). Below the specified noise level at 1 Hz, the electrical noise floor increases approximately inversely with frequency. Since the high pass filtering and analog integration are deterministic processes with respect to the ips domain, the fundamental noise floor can readily be transformed to the ips domain.

The total noise floor (most probable noise floor) will be a linear combination of the minimal sensor noise floor discussed above, the noise introduced by temperature transients experienced by the sensor 24, and any other noise that is introduced. These additional noise sources will vary with sensor type, sensor location, and other factors that are difficult to predict. Therefore, the preferred procedure to establish the most probable noise floor is:

1. Obtain the averaged spectral data (output of averager 40 shown in FIG. 1) in the velocity domain with a user defined measurement parameter set;
2. Find a set of minimum velocity spectra data points;
3. Fit the minimum velocity spectra data points with a quadratic function; and
4. Add 1σ (1 standard deviation) to the quadratic fit curve at all frequencies to establish the most probable noise floor.

The quadratic fit curve is preferably obtained by choosing minimum data points over predefined ranges of the velocity spectra data, and then performing a quadratic fit to those data points. This process is repeated for all segments of the velocity spectra data to obtain the quadratic fit curve.

For example, but not way of limitation, assume that a 400 line spectra is produced over a frequency range of 0.0 to 10.0 Hz. Each line in the spectra is separated from the other lines by 0.025 Hz. In accordance with the present invention, a minimum data point would be found, first, in the range of zero to 0.25 Hz (for example), then 0.25 to 0.50 Hz, etc., until minimums are found for the entire data range. In each 0.25 Hz segment, ten data points are analyzed to find the minimum. Then, a quadratic fit curve is fitted to the minimum data points and 1σ (one standard deviation) is added to the curve to establish the most probable noise floor. The threshold noise floor, as previously discussed, is then calculated by adding an additional 3σ to the most probable noise floor. It should be reiterated that the above noise floor calculations are exemplary only and present one example of how the most probable noise floor for the present invention might be determined.

The standard deviation calculation is from general noise analysis theory. Namely, the fractional standard deviation ($\sigma_F$) is given by the equation:

$$\sigma_F = \frac{1}{\sqrt{BT}} \qquad (3)$$

where:

B is bandwidth in Hz; and

T is analysis time in seconds.

In the case of Bartlett window and 1 block averaging, $\sigma_F=1$. If a Hanning window is being used, $\sigma_F=\frac{1}{2}^{1/2}$ or 0.71. For the case where block Hanning averaging is employed, the fractional deviation for averaged results is given by the equation:

$$\bar{\sigma}_F = \frac{0.71}{\sqrt{n}} \qquad (4)$$

where:

n is the number of blocks which could be taken in the allotted time without overlapping.

For example, when employing a 3 block, 67% overlap averaging, n is given by the equation:

$$n = 1 + (n-1)\left(1 - \frac{\% \text{ overlapping}}{100}\right) \qquad (5)$$

or $$n = 1 + (2)\left(\frac{1}{3}\right) = 1\frac{2}{3}. \qquad (6)$$

If P(f) represents the most probable noise floor, then the threshold for a specified confidence level is obtained by adding the appropriate number of $\_\sigma_F$'s to P(f), as illustrated the following equation:

$$\text{ConfidenceLevelThreshold}(f) = P(f)\left(1 + \frac{0.71y}{\sqrt{n}}\right) \qquad (7)$$

where:

y=1 for 67% confidence level;

y=2 for 90% confidence level;

y=3 for 95% confidence level, etc.

In a preferred embodiment, a 95% confidence level is employed. The spectral data is compared to the specified threshold noise floor by comparator 46 and any spectral data point which exceeds the 95% confidence level is accepted as vibration induced (significant) and subsequently corrected by a corrector function, shown generally at 48, for the attenuation introduced by the three single pole, high pass filters 50–54. An additional single pole, high pass filter (not shown) introduced by the electronics housed within the sensor 24 can also be included. In addition to correcting any spectral data point exceeding the threshold noise floor, those data points that are nearest to a significant data point are also corrected so that the algorithm employed to interpolate where the spectral data point (significant amplitude) falls in frequency can be applied to the corrected spectral data point.

If the desired output of the analysis is displacement, digital integration may be employed on the corrected amplitudes. Alternatively, a second analog integrator (not shown) may be employed prior to the autoranging amplifier 32 to transform the vibration signal from the velocity domain to the displacement domain.

The following test results are presented as Examples to help illustrate that, using the present invention, significant improvements in dynamic range are gained using the SST methodology disclosed herein. This improvement greatly improves the analyst's ability to execute meaningful vibration analysis on slow speed machinery.

EXAMPLE A

Tests were conducted on a variable, slow speed, test rotor kit with an adjustable cam (used for displacement) by employing the SST methodology of the present invention. The rotor kit was configured to provide reference displacement of 9 to 9.5 mils p—p in the 15 to 150 rpm range. The sensor was a 500 mV/g shear mode, low noise accelerometer. The data collector/analyzer (a CSI 2120 analyzer employing a 16-bit delta-sigma A/D converter) was set up to perform integration of the accelerometer signal by using a 4-block nonoverlapping average, an analysis bandwidth of 10 Hz, and a 400-line spectra.

Figure 3:
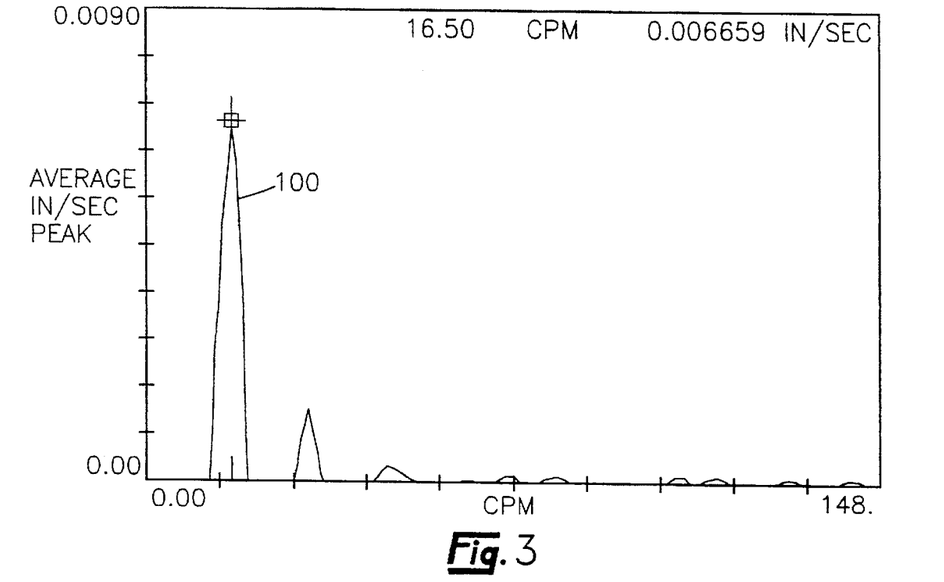
FIG. 3 is an averaged spectrum of test data obtained from test rotor kit using analog integration of the data with correction of distortion caused by the integration.

FIG. 3 presents an average transformation of the data to the frequency domain by employing the SST methodology to process the vibration signal produced by the accelerometer. In other words, the following three steps of the SST methodology were taken in processing the vibration signal:

1. The raw signal from the accelerometer was integrated and then transformed to the frequency domain.
2. Four frequency domain transformations of the data were averaged and a threshold noise floor was established based on a statistical 95% confidence level; and
3. Data judged as vibration induced (exceeded the 95% confidence level, or noise floor) was corrected for signal distortion introduced by the analog integrator.

The results presented in FIG. 3 are in velocity unit—inches per second-peak (ips-peak). The 6.7 mil ips-peak at 16.5 CPM (0.275 Hz), as indicated by reference character 100, is 7.8 mils p—p. The sensor used had a 3 dB point at 0.2 Hz. Correcting the 7.8 mils p—p for the sensor response leads to 9.6 mils p—p as the measured response.

Figure 4:
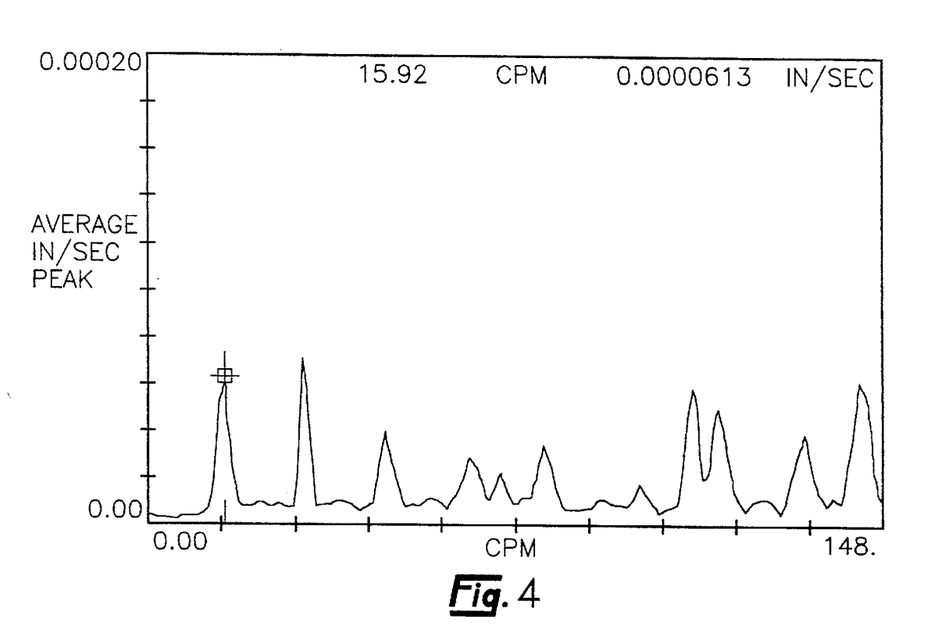
FIG. 4 is an averaged spectrum of test data obtained from the test rotor kit of FIG. 3 using analog integration without correction for distortion.
Figure 5:
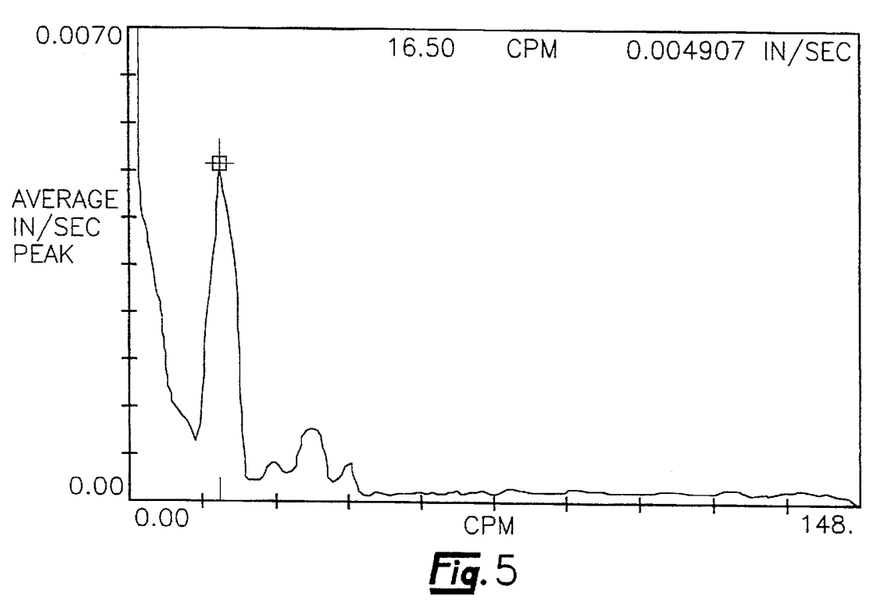
FIG. 5 is an averaged spectrum of test data obtained from the test rotor kit of FIG. 3 using digital integration.

FIG. 4 presents the results of an average transformation to the frequency domain using straight analog integration without correction for distortion. FIG. 5 presents the results of an average transformation to the frequency domain using digital integration. As FIG. 4 illustrates, the distortion contributed by the analog integrator prevents the lower frequency peaks from dominating the spectra. From these results, one may argue that the statistical analysis is not necessary. However, there are many situations that arise when monitoring slow speed machinery where the decision of whether a specific peak is clearly mechanically-induced or randomly occurring is not so obvious. Of course, the straight digital integration of FIG. 5 provides results that are not subject to the analog integrator distortion, but as will be shown below with regard to Example B, loss of dynamic range can become a serious limitation to the digital integration procedure which destroys confidence in the accuracy of the analysis.

EXAMPLE B

A small gear box similar to that illustrated at 22 in FIG. 1 was chosen to demonstrate the limitations resulting from loss of dynamic range caused by the A/D converter. The gear box chosen was a speed-reduction component being driven by a DC motor. Attached to the inlet shaft was a 16-tooth pinion driving an 88-tooth gear mounted on an intermediate shaft. Attached to the intermediate shaft was a 17-tooth pinion driving a 54-tooth gear on the output shaft. For the results presented herein, the output shaft was turning at an approximate speed of 60 rpm. The sensor used was a 500 mV/g shear mode, low noise accelerometer.

Figure 6:
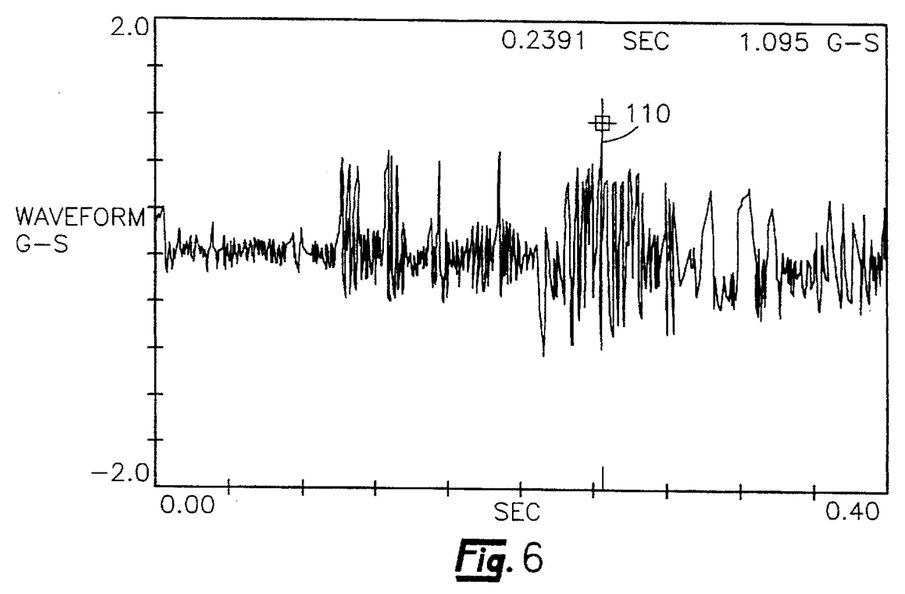
FIG. 6 is a broadband time trace in g's of an accelerometer output mounted on a gear box from which data presented in FIG. 7 and FIG. 8 were taken.

FIG. 6 presents a time trace in g's per second of the accelerometer output with the analyzer set for a 1000 Hz bandwidth and a data block size of 1024 sample points. The maximum signal level 110 was slightly greater than 1 g. This suggests that the autoranging function of the analyzer (a CSI 2120 analyzer employing a 16-bit delta-sigma A/D converter) selected a 2 g full-scale range for the A/D converter.

Figure 7:
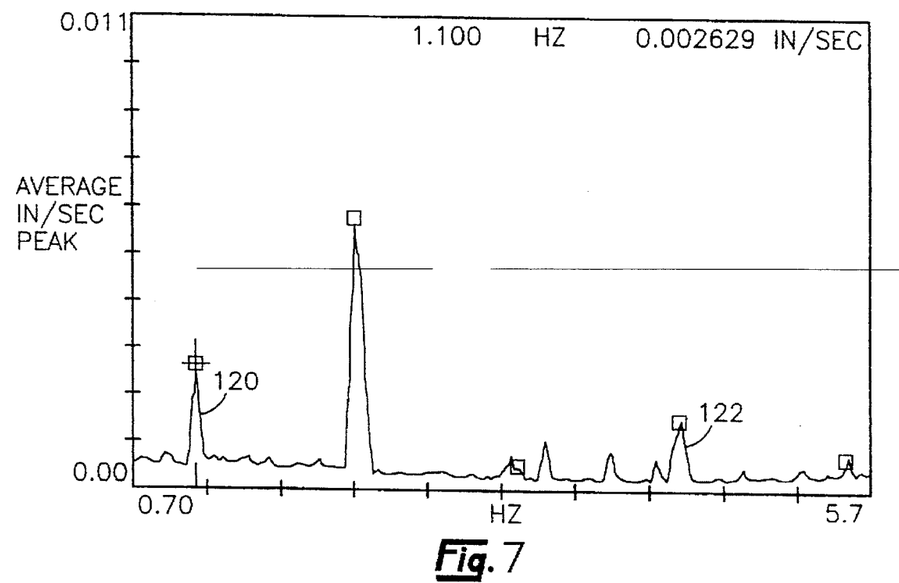
FIG. 7 is an averaged spectrum of test data taken from measurements of the gear box referenced in FIG. 6 using analog integration with correction of distortion caused by the integration.

The analyzer was configured to detect small mechanical vibrations in the gear box at one times (1×) the slow speed shaft (output shaft). FIG. 7 presents the results for a 4-block, nonoverlapping-average, 10 Hz bandwidth, and 400-line spectra employing the SST methodology (with analog integrator) of the present invention. As FIG. 7 illustrates, the 1× component from the slow speed shaft is clearly detectable at 1.1 Hz as seen by peak 120. This amplitude, or peak 120 corresponds to a 0.76 mil p—p vibration at 1.1 Hz.

Figure 8:
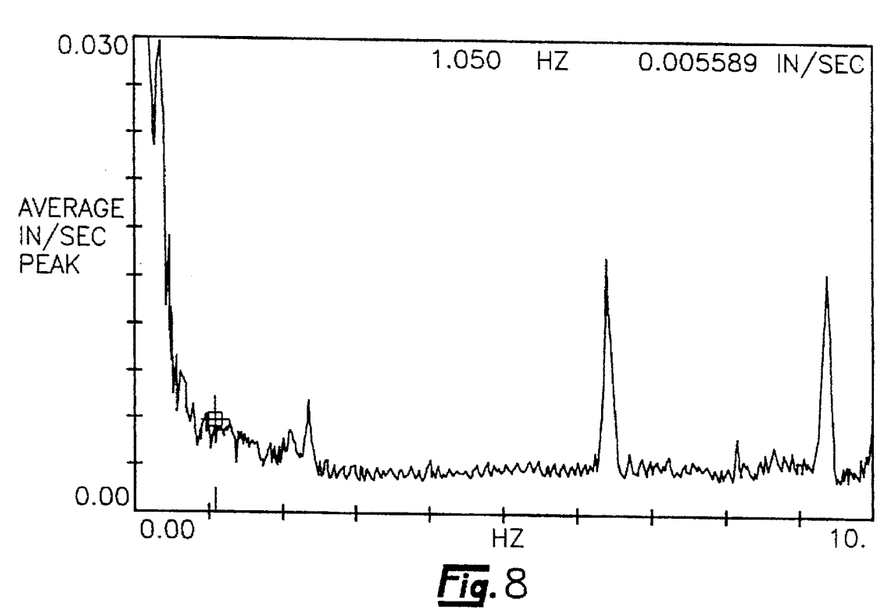
FIG. 8 is an averaged spectrum of test data obtained from the gear box of FIG. 6 using digital integration.

The test used to acquire the data presented in FIG. 7 was repeated using digital integration to produce the results shown in FIG. 8. As can be seen, the 1.1 Hz peak of FIG. 7 is not present in FIG. 8 due to the fact that the dynamic range of the A/D converter was insufficient to resolve such a small signal level. The accelerometer time trace of FIG. 6 shows the broad band signal from the accelerometer had a peak acceleration level slightly above 1 g. The probable full scale range of the A/D converter was in the 2 to 3 g range (assume 2.5 g's). Using 2.5 g's as the A/D converter range, the 1× component at 1.1 Hz shown in FIG. 7 (which is equivalent to 42 μg's-peak) is at −95 dB. The 2× component in FIG. 7 (peak 122) is at −88 dB. As previously described, the A/D converter employed by the analyzer was a 16 bit, delta-sigma device with minimal bit stutter. The expected noise floor due to bit stutter of the A/D converter would be in the 90 dB range which is sufficient to overwhelm peak 120 shown in FIG. 7. This explains why the 1.1 Hz peak 120 of FIG. 7 obtained by analog integration is not present in the digital integration measurement of FIG. 8. As this test clearly shows, loss of dynamic range can become a serious limitation to the digital integration procedure.

It is contemplated, and will be apparent to those skilled in the art from the foregoing specification, drawings, and examples that modifications and/or changes may be made in the embodiments of the invention. Accordingly, it is expressly intended that the foregoing are illustrative of preferred embodiments only, not limiting thereto, and that the true spirit and scope of the present invention be determined by reference to the appended claims.

What is claimed is:

1. A method of processing vibration signals to produce information corresponding to mechanical vibration in slow speed machinery, the method comprising the steps of:

producing a vibration signal measured in acceleration units corresponding to mechanical vibration generated by slow speed machinery, said vibration signal including amplitudes corresponding to frequencies below a pivot frequency, amplitudes corresponding to frequencies above the pivot frequency, and noise;

distorting the vibration signal by analog integration so that amplitudes corresponding to frequencies below the pivot frequency are amplified and amplitudes corresponding to frequencies above the pivot frequency are attenuated, thereby producing a distorted vibration signal measured in velocity units;

digitizing the distorted vibration signal during a predetermined time interval to produce a time series of digital vibration signals measured in velocity units;

producing a first preliminary output in the frequency domain corresponding to the time series of digital vibration signals;

calculating a most probable noise floor;

comparing the amplitudes of the first preliminary output to the most probable noise floor;

eliminating amplitudes in the first preliminary output that are below the most probable noise floor to produce a second preliminary output; and correcting the second preliminary output by a correction function that inversely corresponds to the distorting of the analog integration to produce a final output corresponding to mechanical vibration generated by the slow speed machinery.

2. The method of claim 1, wherein said calculating step further comprises the steps of:

determining a plurality of minimum amplitudes in a plurality of segments of the first preliminary output;

fitting minimum amplitudes of the first preliminary output with a quadratic function to produce a quadratic fit curve; and adding one standard deviation to the quadratic fit curve at all frequencies to produce the most probable noise floor.

3. The method of claim 1 wherein said step of producing a first preliminary output comprises the step of converting the time series of digital vibration signals to the frequency domain to produce a distorted vibration spectrum constituting the first preliminary output.

4. The method of claim 3, wherein said converting step further comprises the steps of:

transforming the time series of digital signals to the frequency domain by means of a fast Fourier transform to produce a series of spectra; and producing a single spectrum from the series of spectra, said single spectrum having a plurality of amplitudes and frequencies with each of said amplitudes corresponding to a unique one of the frequencies, said amplitudes corresponding to mechanical vibration produced by the slow speed machinery.

5. The method of claim 4, further comprising averaging the series of spectra to produce an averaged spectrum as the single spectrum.

6. The method of claim 1, further comprising the step of calculating a threshold noise floor based on a statistical variance of the most probable noise floor.

7. The method of claim 6 wherein said statistical variance is a three sigma statistical variance of the most probable noise floor.

8. The method of claim 1, further comprising the step of eliminating a predetermined range of frequencies and corresponding amplitudes from the distorted vibration signal.

9. The method of claim 1, further comprising the step of eliminating a predetermined range of frequencies and corresponding amplitudes from the vibration signal.

10. The method of claim 1 wherein said distorting step comprises integrating the vibration signal to produce an integrated signal and integrating the integrated signal to produce a double integrated signal constituting the distorted vibration signal as measured in displacement units.

* * * * *